(12) United States Patent
Lederman et al.

(10) Patent No.: US 9,027,698 B2
(45) Date of Patent: May 12, 2015

(54) HEARING ASSISTANCE DEVICE AND METHOD

(71) Applicants: Jo Ann Lederman, Coral Gables, FL (US); Agustin Arrieta, Miami, FL (US)

(72) Inventors: Jo Ann Lederman, Coral Gables, FL (US); Agustin Arrieta, Miami, FL (US)

(73) Assignee: JAG Hearing, LLC., Miami, FL (US)

( * ) Notice: Subject to any disclaimer, the term of this patent is extended or adjusted under 35 U.S.C. 154(b) by 0 days.

(21) Appl. No.: 14/188,860

(22) Filed: Feb. 25, 2014

(65) Prior Publication Data

US 2014/0224568 A1  Aug. 14, 2014

Related U.S. Application Data

(63) Continuation-in-part of application No. 13/654,985, filed on Oct. 18, 2012, now Pat. No. 8,657,063, which is a continuation-in-part of application No. 13/353,899, filed on Jan. 19, 2012, now Pat. No.

(Continued)

(51) Int. Cl.
*H04R 25/00* (2006.01)
*A61F 11/00* (2006.01)

(52) U.S. Cl.
CPC ..................... *A61F 11/008* (2013.01)

(58) Field of Classification Search
CPC ....................................................... H04R 25/00
USPC .......................................................... 181/129
See application file for complete search history.

(56) References Cited

U.S. PATENT DOCUMENTS

| 850,978 A | 4/1907 | Soares |
| 1,043,924 A | 11/1912 | Gottlieb |
| 1,292,083 A | 1/1919 | Sawyer |
| 1,820,107 A | 8/1931 | Agee |

(Continued)

FOREIGN PATENT DOCUMENTS

| DE | 322912 C | 7/1920 |
| JP | 2014-510552 | 5/2014 |

(Continued)

OTHER PUBLICATIONS

Everest, Alton, Master Handbook of Acoustics, Fourth Edition, 2001, [retrieved on Jul. 18, 2012], Retrieved from the Internet: <htlp://wiki.dxarfs.washington.edu/sandbox/groups/general/wiki/9e11/attachmentsO12ef/The%20eer%20and%2Othe%20perception%-20o-%20sound%2o-%20Alton%20Everest%20%28-from%20The%20Master%20Handbook%20Of%Acoustics%29.pdf?sessionID=c8b741b338b88cf7541bd02f23o6d9310610b6da>, Chapter 3, pp. 43-44.

(Continued)

*Primary Examiner* — Forrest M Phillips
(74) *Attorney, Agent, or Firm* — Malloy & Malloy, P.L.

(57) ABSTRACT

A device and attendant method to assist the hearing of a user by being removably connected to and disposing a user's ear in an enhanced hearing orientation. The device includes an elongated base, which may be disposable, and has a sufficient length to be disposed in an operative position behind the user's ear. Opposite ends of the base include an adhesive material secured to a common side thereof, wherein different ones of said opposite ends are respectively disposed and maintained in confronting engagement with a rear surface of the ear and adjacently disposed portion of the user's head. The base further includes biasing capabilities disposed and structured to exert a sufficient, forwardly and outwardly directed force on the user's ear to dispose and maintain it in the enhanced hearing orientation, when the base is in the operative position.

15 Claims, 7 Drawing Sheets

Related U.S. Application Data 8,424,634, which is a continuation-in-part of application No. 13/353,865, filed on Jan. 19, 2012, now Pat. No. 8,360,198, which is a continuation-in-part of application No. 13/353,817, filed on Jan. 19, 2012, now Pat. No. 8,371,418, which is a continuation-in-part of application No. 13/214,911, filed on Aug. 22, 2011, now Pat. No. 8,230,965, which is a continuation-in-part of application No. 13/011,506, filed on Jan. 21, 2011, now abandoned.

(56) References Cited

U.S. PATENT DOCUMENTS

| | | |
|---|---|---|
| 1,950,839 A | 3/1934 | Chirila |
| 2,001,862 A | 5/1935 | Battey |
| 2,398,073 A | 4/1946 | Bonde |
| 2,443,481 A | 6/1948 | Sene |
| 2,509,157 A | 5/1950 | Lind |
| 2,537,201 A | 1/1951 | Amfitheatrof |
| 2,566,148 A | 8/1951 | Sky |
| 2,586,219 A | 2/1952 | Geffas |
| 2,625,931 A | 1/1953 | Phillips |
| 3,046,989 A | 7/1962 | Hill |
| 3,141,459 A | 7/1964 | Orcutt |
| 3,426,751 A | 2/1969 | Radewan |
| 3,531,090 A | 9/1970 | Laible |
| 3,742,943 A | 7/1973 | Malmin |
| 3,835,848 A | 9/1974 | Berner |
| 3,935,859 A | 2/1976 | Doyle |
| 3,976,066 A | 8/1976 | McCartney |
| 4,000,737 A | 1/1977 | Horn |
| 4,153,051 A | 5/1979 | Shippert |
| 4,159,021 A | 6/1979 | Casburn |
| 4,187,838 A | 2/1980 | Dubrowski |
| 4,213,452 A | 7/1980 | Shippert |
| 4,274,402 A | 6/1981 | Shippert |
| 4,275,715 A | 6/1981 | Wolfe |
| 4,340,040 A | 7/1982 | Straith |
| 4,402,314 A | 9/1983 | Goode |
| 4,414,977 A | 11/1983 | Rezakhany |
| 4,534,342 A | 8/1985 | Paxa |
| 4,674,133 A | 6/1987 | Oschner |
| 4,768,613 A | 9/1988 | Brown |
| 4,771,859 A | 9/1988 | Breland |
| 4,823,789 A | 4/1989 | Beisang, III |
| 4,890,688 A | 1/1990 | Baker |
| 4,905,681 A | 3/1990 | Glascock |
| 4,932,943 A | 6/1990 | Nowak |
| 4,971,282 A | 11/1990 | Dickinson |
| 4,974,430 A | 12/1990 | Turner |
| 4,984,302 A | 1/1991 | Lincoln |
| 4,995,114 A | 2/1991 | Price, Jr. |
| 5,003,971 A | 4/1991 | Buckley |
| 5,020,629 A | 6/1991 | Edmundson et al. |
| 5,022,389 A | 6/1991 | Brennan |
| 5,476,091 A | 12/1995 | Johnson |
| 5,533,499 A | 7/1996 | Johnson |
| 5,533,503 A | 7/1996 | Doubek et al. |
| 5,549,103 A | 8/1996 | Johnson |
| 5,920,636 A | 7/1999 | Oliveira et al. |
| 5,965,850 A | 10/1999 | Fraser |
| 6,039,751 A | 3/2000 | Hardee |
| 6,318,362 B1 | 11/2001 | Johnson |
| 6,817,440 B1 | 11/2004 | Kim |
| 7,028,343 B1 | 4/2006 | Watson |
| 7,093,600 B2 | 8/2006 | Sorribes |
| 8,122,995 B1 | 2/2012 | Riley |
| 8,230,965 B1 * | 7/2012 | Lederman et al. ............ 181/129 |
| 8,360,198 B2 | 1/2013 | Lederman et al. |
| 8,371,418 B2 | 2/2013 | Lederman et al. |
| 8,424,634 B2 | 4/2013 | Lederman et al. |
| 8,657,063 B2 | 2/2014 | Lederman et al. |
| 2006/0151236 A1 | 7/2006 | McCool |
| 2007/0074991 A1 | 4/2007 | Heisserer |
| 2010/0059078 A1 | 3/2010 | Winters |

FOREIGN PATENT DOCUMENTS

| | | |
|---|---|---|
| WO | WO2006/029624 | 3/2006 |
| WO | WO2012/100121 | 7/2012 |

OTHER PUBLICATIONS

Everest, Alton. Master Handbook of Acoustics, Fourth edition. 2001 [retrived on Jul. 18, 2012]. retrieved from the internet <http://wild.dxarts.washington.edu/sandbox/groups/general/wiki/9ellb.attachments/012er/the%20ear%20and%20the%20perception%2-0of%20sound%207%20Alton%20Everest%20%28from%20-The%20Master%Handbook%20of%20acoustics%29.pdf?sessionID=c8b741b338ob8of8541bd02f23e6d93108106da>. Chapter 3, pp. 43-44.

* cited by examiner

HEARING ASSISTANCE DEVICE AND METHOD

CLAIM OF PRIORITY

The present application is a continuation-in-part application filed, having Ser. No. 13/654,985, filed on Oct. 18, 2012, which matured into U.S. Pat. No. 8,657,063, which is a continuation-in-part application of previously filed application, having Ser. No. 13/353,899 filed on Jan. 19, 2012, which matured into U.S. Pat. No. 8,424,634 on Apr. 23, 2013, which is a continuation-in-part application of previously filed application, having Ser. No. 13/353,865 filed on Jan. 19, 2012, which matured into U.S. Pat. No. 8,360,198 on Jan. 29, 2013, which is a continuation-in-part application of previously filed application, having Ser. No. 13/353,817 filed on Jan. 19, 2012, which matured into U.S. Pat. No. 8,371,418 on Feb. 12, 2013, which is a continuation-in-part application of previously filed application, having Ser. No. 13/214,911 filed on Aug. 22, 2011, which matured into U.S. Pat. No. 8,230,965 on Jul. 31, 2012, which is a continuation-in-part application of previously filed application, having Ser. No. 13/011,506, filed on Jan. 21, 2011, all of which are incorporated herein by reference in their entirety.

BACKGROUND OF THE INVENTION

1. Field of the Invention

This invention is directed to a hearing assistance device disposed and structured to be removably secured in an operative position behind the ear of the user. The device may be structured for repeated reuse or for disposable after one or a relatively few uses and includes biasing capabilities structured to exert a sufficient, forwardly and outwardly directed force on the ear to dispose and maintain it in an enhanced hearing orientation, when the hearing assistance device is in the operative position.

2. Description of the Related Art

Modern day hearing aids are typically electroacoustic devices which fit in or behind a wearer's ear. As such, devices of this type are designed to amplify and modulate sound for the wearer. Moreover, every modern day electronic hearing aid comprises operative components including a microphone, loud speaker or receiver, battery and electronic circuitry. The electronic circuitry varies among devices and generally falls into different categories based on the type of audio processing (either analog or digital) and the type of control circuitry such as being adjustable or programmable.

Accordingly, modern technology has developed the electronic hearing aid to the point where the hearing impaired are no longer significantly disadvantaged in terms of interpreting speech and ambient sound. However, in earlier times such modern, electronic devices were, of course, not available. Instead, the individual who had difficulty hearing frequently relied on mechanical devices, such as, an "ear trumpet" or "ear horn". These devices were passive, funnel-like amplification cones designed to gather sound energy and direct it into or towards the ear canal. Modern day devices working on the same principal may generally include bone anchored hearing aids and/or cochlear implants. However, as previously used the "horn type" hearing aids included a tapered sound guide having an enlarged open end used to receive and optimize the transfer of sound from the air to the individual.

Additional developments in hearing aid technology have also led to relatively inexpensive disposable hearing aids powered by non-replaceable batteries. This type of hearing aid structure is designed to use power sparingly so that the included non-replaceable battery lasts for a reasonable length of time but for a much shorter duration than traditional hearing aids. Accordingly, disposable hearing aids are meant to overcome the task of battery replacement and other maintenance requirements such as adjustment, cleaning, programming, etc. Today a limited number of such disposable hearing aids are commercially available and are usable in different ways by the consumer.

Accordingly, there is a need in this industry for a hearing aid which is extremely inexpensive, functional to at least minimally increase the ability to hear ambient sounds and speech and which can be easily applied, removed, replaced, etc. when so desired. Such an improved, mechanical, and/or disposable hearing aid could be made available in standard or varied sizes, so as to be available to individuals of different ages/sizes, and also be structured to be applied in an operative position behind the ear of a wearer. Moreover, a preferred and proposed hearing aid of the type described could be extremely light weight and have an overall dimension and configuration which would allow a wearer or a user to substantially ignore its existence when conducting normal, everyday activities.

Therefore, in operation such a preferred and proposed mechanical hearing aid would facilitate reception of sound waves when disposed and maintained in an enhanced hearing orientation. Further, the overall structural and operational features of such a proposed mechanical hearing aid would provide a safe and relatively unobtrusive repositioning of the ear without discomfort or embarrassment of the user.

SUMMARY OF THE INVENTION

The present invention is directed to a device structured to mechanically assist the hearing ability of a user by the forced positioning and maintenance of the user's ear into an "enhanced hearing orientation", when the device is disposed in an operative position behind the user's ear. More specifically, the various preferred embodiments of the hearing assistance device of the present invention include a base having a substantially elongated configuration of sufficient length to be disposed in the operative position relative to the user's ear. The base further includes opposite ends and an adhering structure or material, such as an adhesive composition, disposed on a common side or common surface which is at least adjacent to the opposite ends. Alternately, the adhering composition can extend substantially along the entire length or at least a majority of the length of one side. Moreover, when used, the adhesive material composition is hypoallergenic and as such, does not cause irritation or damage to the skin of the user to which the base is attached, even when disposed in the operative position for a relatively prolonged period of time.

Disposition of the base in the aforementioned operative position is dependent, at least in part, on the dimension, configuration and overall structure of the base. As such, the operative position comprises different ones of the opposite ends of the base being concurrently disposed into removable, confronting engagement with a rear surface of the ear and a correspondingly disposed and/or adjacent portion of the head of the user. In the preferred operative position, the opposite ends are removably attached in overlying relation to a bone or hard tissue portion located behind and adjacent to the ear. Moreover, this adjacent, hard tissue portion of the head may include the temporal/mastoid portion of the user's skull.

As will be explained in greater detail hereinafter, the base will be attached to the outer skin surface of a rear portion of the ear as well the outer skin of the adjacent hard tissue portion of the head. As a result, biasing capabilities associated with the base serve to exert a sufficient, outwardly directed force on the ear and a resultant positioning of the ear in the "hearing enhanced orientation". More specifically, the disposition of one of the opposite ends in overlying at least partially supported relation to the "relatively unyielding" hard tissue portion of the user's head, facilitates the exertion of a sufficient, outwardly directed, force on the comparatively more flexible ear Accordingly, the various preferred embodiments of the hearing assistance device of the present invention include a base structured to have biasing capabilities. Moreover, the biasing capabilities of the base are disposed and structured to exert a "pushing" force concurrently on both the ear and the adjacent, hard tissue portion of the head. As a result, when the base of the hearing assistance device of the present invention is in the aforementioned operative position, the ear associated with the device will be "pushed" or forced outwardly from the adjacent head portion and forwardly towards the face or other frontal portion of the head into an orientation which significantly enhances the individual's ability to hear. The "enhanced hearing orientation" of the user's ear, when influenced by the subject hearing assistance device, is analogous to an individual placing his or her hand behind the ear in a substantially "cupped" configuration. This commonly applied cupping action by an individual with hearing difficulties disposes the ear in a more receptive orientation to receive directed and ambient sounds, thereby enhancing the individual's ability to hear.

Other structural and operative features of the various preferred embodiments of the present invention include at least one of the two opposite ends of the base having an enlarged configuration and dimension, at least partially defined by an increased width or transverse dimension thereof. Alternatively, each of the opposite ends may have substantially equivalent dimensions and configurations. In this latter embodiment the biasing capabilities of the base may be increased or at least be predetermined to exert a sufficient force on the ear to force it outwardly and forwardly into the enhanced hearing orientation. For purposes of comfort, as well as practicality, the base further includes an intermediate portion which may be substantially equal in dimension to at least one of the opposite ends. However, in at least some of the embodiments of the hearing assistance device, the intermediate portion of the base typically has a lesser transverse dimension than the one opposite end disposed in confronting engagement with the rear surface of the head, when the base is in the operative position on an individual.

Therefore, the possible differences in dimension and configuration of the opposite ends and intermediate portions of the base enhance the versatility and efficiency in applying the hearing assistance device in the operative position on an individual. However, one preferred embodiment of the present invention comprises the operative position of the base being defined by the larger opposite end being disposed in confronting engagement with the hard tissue portion of the head, behind the ear. This larger opposite end portion may have a predetermined configuration such as, but not limited to, a semi-circular peripheral configuration. In cooperation therewith the smaller or similarly dimensioned and configured other opposite end will be removably connected to the corresponding rear surface portion of the ear. This operative position will, along with the predetermined biasing capabilities of the base, assure the exertion of a sufficient, forwardly and outwardly directed force on the ear, due at least in part to the greater flexibility of the ear and the comparatively unyielding characteristics of the adjacent hard tissue portion of the head.

The adequacy of the pushing force, concurrently exerted on the ear and the adjacent hard tissue portion of the head is determined by the inherent strength of the biasing capabilities associated with the base. Therefore, one preferred embodiment of the present invention includes the biasing capabilities being defined by at least one substantially elongated biasing member having "an inherent bias" and extending along at least a majority or substantially the entire length of the base. In contrast, additional preferred embodiments of the present invention may be defined by the base being formed, in its entirety or in part, from a material having an inherent bias. In either case the pushing force developed by the biasing capabilities of the base are predetermined and/or structured to be sufficient to generate an adequate and concurrently applied pushing force on both the ear and the head, to dispose and maintain the ear in the enhanced hearing orientation, as set forth above.

For purposes of clarity, the term "inherent bias" as referred to herein is meant to include any material, member or structure, which when deformed or disposed out of its naturally assumed orientation, results in the development of a biasing force in the material, member or structure, wherein such developed biasing force tends to orient the material, member or structure, out of the deformed orientation back into its naturally assumed orientation.

Accordingly, the various preferred embodiments of the hearing assistance device of the present invention overcomes many of the disadvantages and problems associated with electronic hearing aids or other mechanical type aids in terms of cost, effectiveness, comfort and convenience. Further, the present invention facilitates the hearing of a user while being relatively unobtrusive. In addition, the hearing assistance device of the present invention may be disposable thereby further facilitating the ability of the user to easily apply, remove, and/or replace the device as desired.

In more specific terms, the biasing capabilities are cooperatively structured with the remainder of the base to define the hearing enhanced orientation as an outwardly and forwardly positioning of the ear relative to the adjacent and/or corresponding portion of the head, such as at least that portion of the head which is engaged by the head segment of the base. Therefore, the base and the biasing capabilities are cooperatively structured to define the hearing enhanced orientation as being dependent on the strength of the positioning force. As cooperatively utilized, the hearing enhanced orientation relative to the user's head is determinative of an increase or decrease in the decibels of the sound pressure level (SPL) of the corresponding ear. Therefore, the farther the ear of the user is disposed outwardly and forwardly from the user's head, the greater the increase in decibel of the sound pressure level, within certain acceptable and/or practical ranges. In cooperation therewith, a reduction or lessening of the forwardly and outwardly positioning of the user's ear, relative to the head, will result in a decrease in the decibels of the sound pressure levels.

Dependent on the hearing capabilities or limitations of the user, the base and the corresponding biasing capabilities may be such as to develop a pushing or positioning force which orients the ear sufficiently outwardly and/or forwardly from the head to establish an increase of at least 5 decibels in the sound pressure level. In the alternative, a pushing or positioning force may be developed which is sufficient to establish an increase of at least 10 decibels in the sound pressure level. Further by way of example, the biasing capabilities of a given base may be structured to create a pushing force sufficient to establish an increase of generally about 20 decibels in the sound pressure level. Therefore, as practically and preferably applied, the base, ear segment and head segment are structured in cooperation with the biasing capabilities to establish a pushing or positioning force which is sufficient to result in an increase of generally between 5 decibels and 20 decibels of the sound pressure level, as compared to the sound pressure level of the ear when it is disposed in a normal orientation, without any pushing or positioning force being exerted thereon. As should be apparent, the needs and/or hearing capacity of the individual utilizing the hearing assistance device will be determinative of an appropriate increase in decibels of the sound pressure level.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying drawings, the present invention is directed to hearing assistance device generally indicated as 10 including an elongated base 12. The base 12 comprises an intermediate portion 14 disposed in interconnecting relation between two oppositely disposed ends 16 and 18. In addition, an adhering structure or material, such as a hypoallergenic adhesive 20, is disposed on an underside of the base 12, which is common to both the oppositely disposed first and second opposite ends 16 and 18 respectively. In the embodiment schematically represented in FIG. 2, the adhering material or adhesive 20 may also extend along substantially the entire length of the corresponding, under surface and thereby extend along at least a portion of the length of the intermediate portion 14.

As also represented, the base 12 has a sufficient length to assume and be disposed in an operative position, as generally represented in FIGS. 3-10, behind ear 100 of a user or wearer of the hearing assistance device 10. As represented, the size of the base 12 in the various embodiments of the hearing assistance device 10 is such as to make it substantially unobservable by a person viewing the corresponding ear 100 from the front and/or side, when disposed behind the ear 100 in an operative position. Accordingly, the dimension and configuration of the base 12 is sufficiently small, relative to the ear 100, to eliminate or at least significantly restrict the possibility the visual detection and/or observation thereof when the device 10 is in the operative position and/or the ear 100 is in an "enhanced hearing orientation" as represented in FIGS. 3-10, and described in greater detail hereinafter.

Further, the provision of the adhering material or adhesive 20 will serve to removably but securely maintain the base 12 in the operative position for relatively prolonged periods of time. However, the adhering characteristics of the material 20 are such as to facilitate removal of the base 12 from the operative position easily and quickly without irritation or damage to the portions of the skin of the user engaged by the base 12.

Additional, structural and operative features of the hearing assistance device 10, specifically including the base 12, comprise the provision of biasing capabilities in the base 12. More specifically, the biasing capabilities are such as to exert a "pushing" force 104 on both the ear 100 and the correspondingly disposed engaged, preferably hard tissue portion of the head 102. Due at least in part to the fact that the ear 100 is more flexible than the corresponding hard tissue portion 102 of the head, the ear 100 is clearly more easily moved or positioned relative to the corresponding portion of the head 102. More specifically, a sufficient, forwardly and outwardly directed force on the ear 100 will dispose it in the "enhanced hearing orientation" as represented in FIGS. 4, 6, 8 and 10. Moreover, the biasing force will be sufficient to maintain the ear 100 in the enhanced hearing orientation for a prolonged period of time, as long as the base 12 is in the operative position behind the ear, as represented in FIGS. 3-10 and explained in greater detail hereinafter.

In more specific terms, the aforementioned biasing capabilities are structured to be incorporated in the base and may take the form of the material 22 from which the base 12 is formed. Therefore, in the embodiment of FIGS. 1 and 2, the material 22 from which the base 12 is formed includes an "inherent bias" which serves to position and maintain the base 12 in a naturally assumed orientation. As such, the naturally assumed orientation of the base 12 may include, but is not limited to, a substantially linear or at least partially planar orientation. However, when the base 12 is selectively disposed in the operative position of FIGS. 3, 5, 7 and 9 it will be partially bent, folded or otherwise forced into a substantially curved or even "u-shaped" configuration as represented, which will accurately be described and referred to herein as a deformed orientation of the base 12. When so deformed, an inherent bias of the base 12 creates a biasing force, which at least partially defines the biasing capabilities of the base 12, is developed. It is further emphasized that the substantially linear or planar configuration of the base 12, 12' when in the naturally assumed orientation is not in tended to describe or be limited to a precise straight line shape and/or flat planar shape. Due to the flexibility of the material from which the base 12 and/or 12' is formed and the various embodiments of the biasing capabilities structured in cooperation therewith, the described "substantially linear" or at least "generally planar" configuration of the base, when in the naturally assumed orientation, should be interpreted accordingly.

Therefore, the biasing capabilities and/or inherent bias of the base 12 is structured to normally bias the base 12 into the aforementioned naturally assumed orientation wherein the base assumes a generally linear or substantially planar orientation. Such an inherently biased material may include various types of plastic, natural or synthetic rubbers or other flexible material compositions which are specifically structured to include the aforementioned inherent bias tending to dispose the base in its naturally assumed orientation such as, but not limited to, that represented in FIG. 2.

Figure 1:
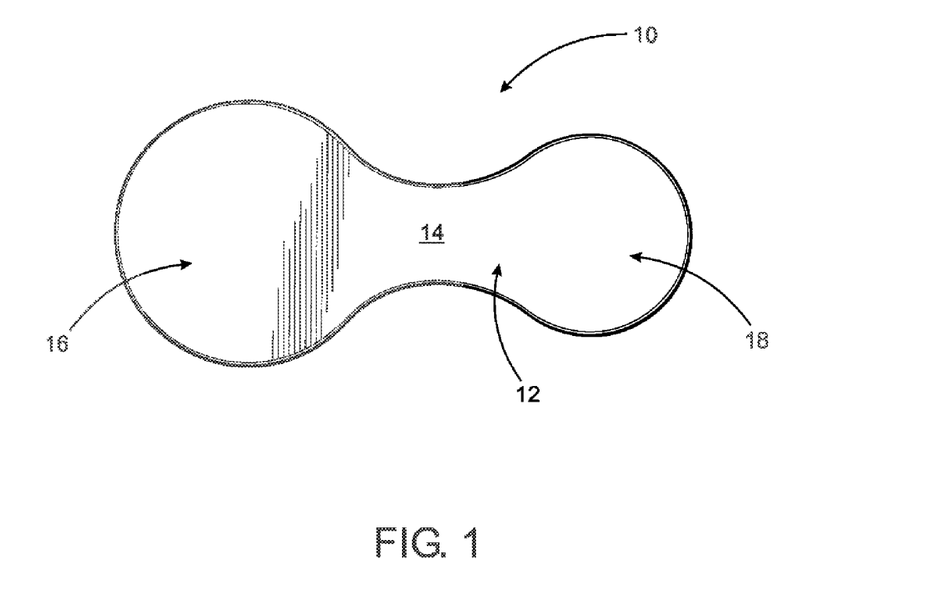
FIG. 1 is a front plan view of one preferred embodiment of the hearing assistance device of the present invention.
Figure 2:
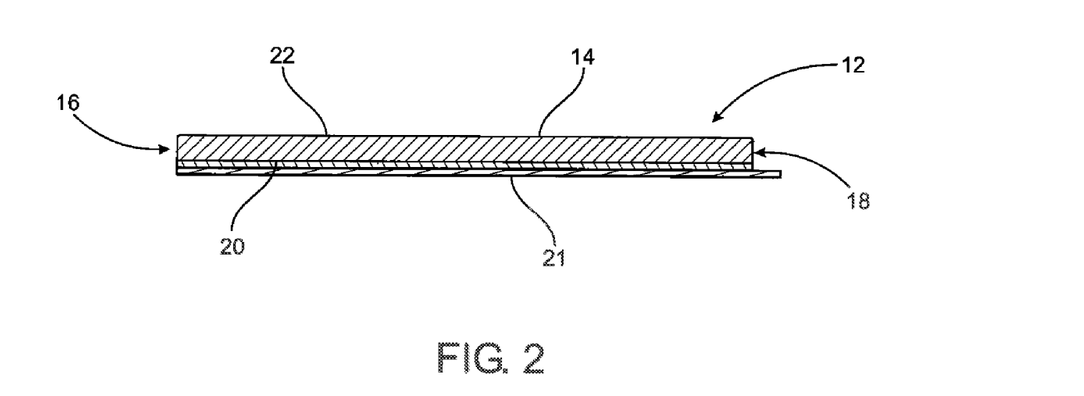
FIG. 2 is a side view along line 2-2 of FIG. 1.
Figure 13:
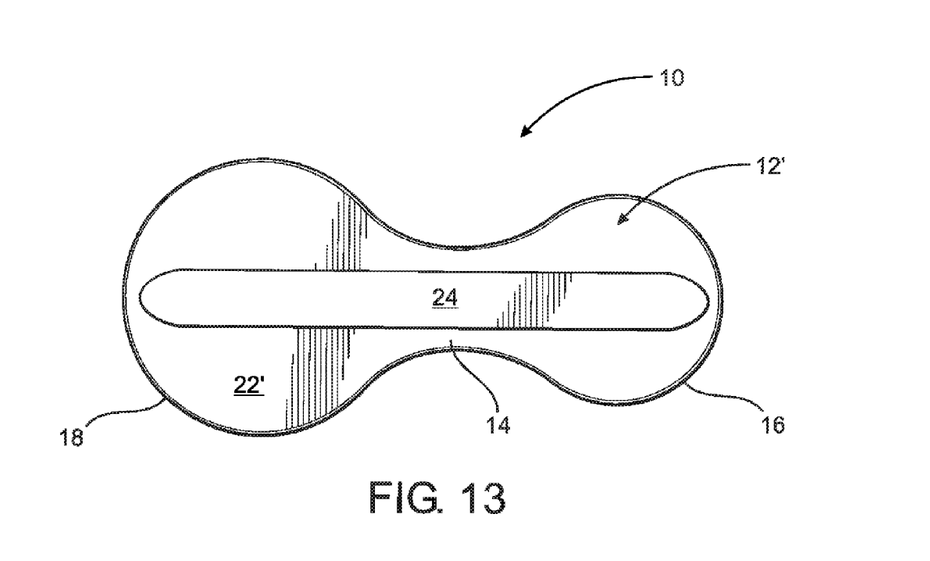
FIG. 13 is a front plan view of yet another preferred embodiment of the hearing assistance device of the present invention.

In contrast the embodiment of FIG. 13 discloses a base 12' formed of a material 22' which may not have the same degree of "inherent bias" as a material 22 from which the embodiments of FIGS. 1 and 2 are formed. As such, the biasing capabilities and inherent bias incorporated within the base 12' comprises a biasing member 24 secured to the base 12'. More specifically, the biasing member 24 has an elongated configuration and is mounted on or within the base 12' so as to extend along at least a majority of the length thereof. Alternatively the biasing member 24 may extend substantially along the entire length, as represented in FIG. 13.

Moreover, the biasing member 24 has the aforementioned "inherent bias" which serves to force the member 24 and the base 12' into its original, substantially linear, in-line or generally planar orientation, as represented in FIG. 2. Structural modifications of the embodiment of FIG. 13 include the biasing member 24 being mounted on or secured to the base 12' by being integrally or fixedly secured to the exterior surface thereof so as to move therewith. Alternatively, the biasing member 24 may be disposed on the interior of the base 12' and be integrally formed therewith during the production or formation of the base 12'. It is emphasized, that while the structural features of the biasing capabilities of embodiments of FIGS. 1, 2 and 9 may vary, as set forth above, the operative features of each of these embodiments are such as to exert a sufficient, forwardly and outwardly directed force on the ear 100 of the user, as schematically represented as 104, when the base 12, 12' is disposed in the operative position of FIGS. 3-6.

Further with regard to the structural and operative features of the base 12 and/or base 12' and for purposes of clarity, the term "inherent bias" as referred to herein is meant to include any material, member or structure, which when deformed or disposed out of its naturally assumed orientation, such as represented in FIG. 2, results in the development of a biasing force in the material, member or structure, wherein such developed biasing force tends to orient the material, member or structure, out of the deformed orientation back into its naturally assumed orientation.

As set forth above and as represented in FIGS. 3-6, one preferred operative position of the base 12, 12' is schematically represented. Moreover, the preferred operative position is more specifically defined by one of the opposite ends, such as the larger, first opposite end 16, being removably but securely disposed in connection and/or confronting engagement with the skin 102' which overlies the hard tissue portion 102 of the user's head located adjacent the back side or the rear surface of the ear 100. In addition, this operative position of the base 12 and/or 12' is further defined by the smaller, second opposite end 18 being removably but securely disposed in confronting engagement with the skin on the back side or the rear surface of the ear 100. It is to be noted that the adjacent hard tissue portion 102 of the head may be more specifically described as the bone which underlies the skin 102' and may be more accurately referred to as the temporal bone and/or the mastoid portion thereof.

Figure 3:
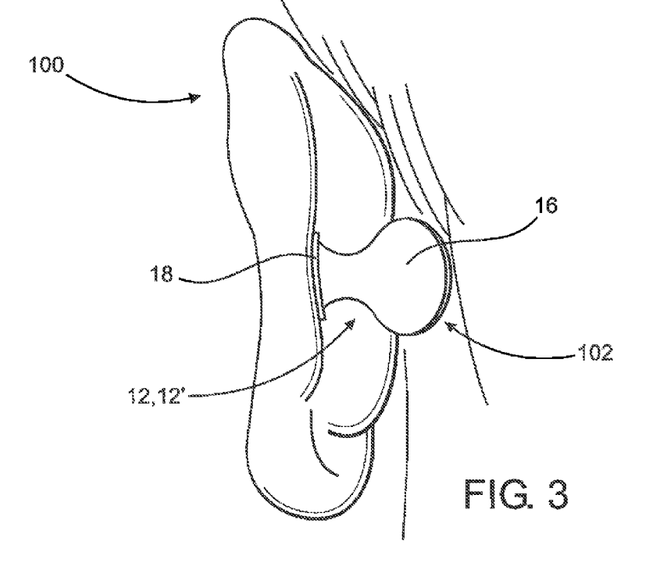
FIG. 3 is a rear view of an embodiment of the hearing assistance device disposed in an operative position behind the user's ear.
Figure 4:
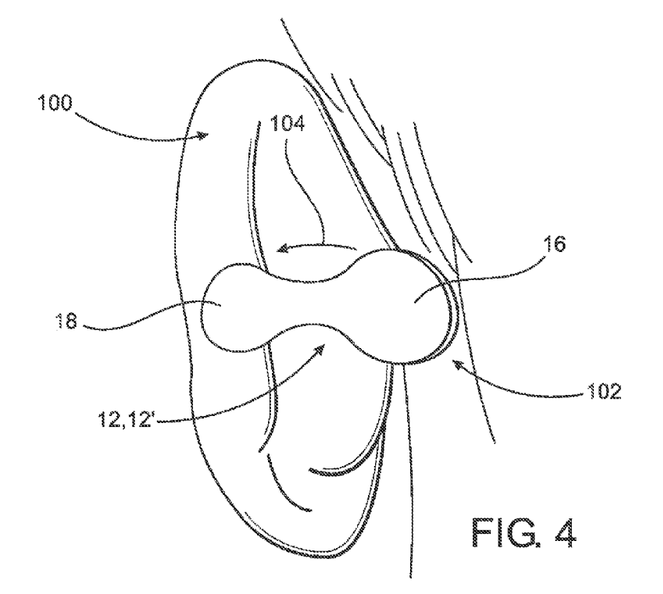
FIG. 4 is a rear view of the embodiment of FIG. 3 wherein the hearing assistance device is concurrently exerting a pushing force on the ear and the head sufficient to dispose the ear in an enhanced hearing orientation.
Figure 5:
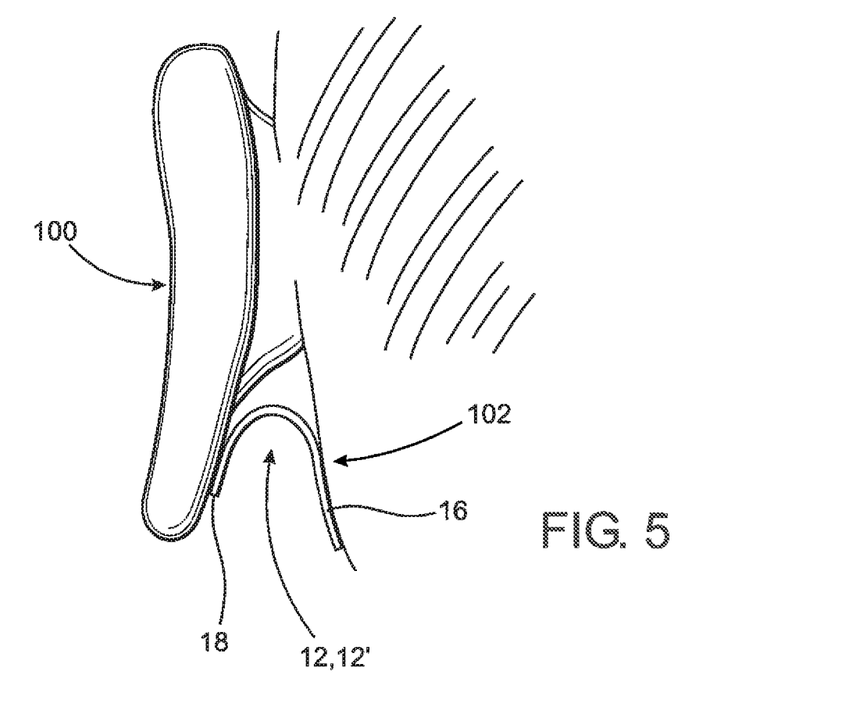
FIG. 5 is a top view of the embodiment of FIG. 3.
Figure 6:
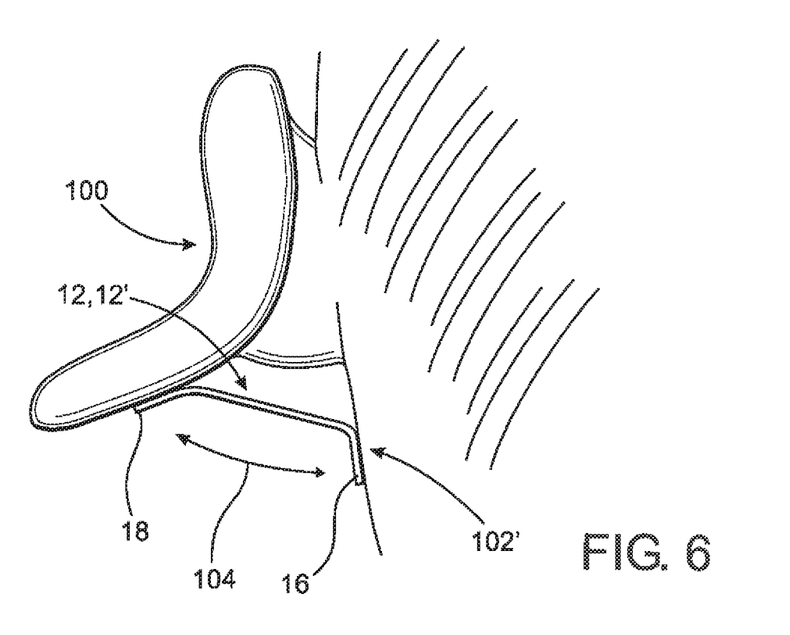
FIG. 6 is a top view of the embodiment of FIG. 4.
Figure 7:
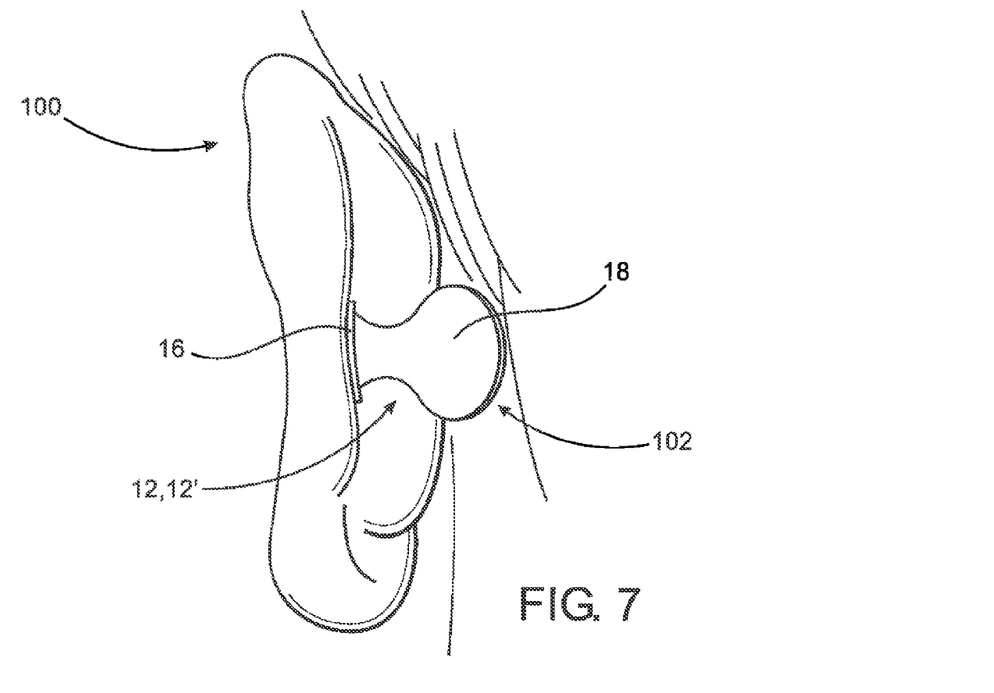
FIG. 7 is a rear view of an embodiment of the hearing assistance device disposed in an operative position behind the user's ear, which differs for the embodiment of FIGS. 3-5.

Therefore, when the base 12, 12' of the hearing assistance device 10 is initially disposed in the operative position, represented throughout the indicated FIGS. 3-6, it may naturally assume a bent, partially folded and/or substantially curved and/or u-shaped configuration, such as represented in FIGS. 3 and 5. However, due to the aforementioned and described inherent bias associated with each of the bases 12 or 12', it will be disposed and structured to concurrently exert a "pushing" force 104 on both the ear 100 and the corresponding hard tissue portion 102 of the head. As set forth above, the inherent flexibility of the ear 100 renders it more easily movable relative to the corresponding hard or boney portion 102 of the head. As a result, the pushing force 104, concurrently exerted on both the undersurface of the ear 100 and the portion 102 of the head, will result in the ear 100 being forced forwardly and outwardly from the head. As a result of the concurrent pushing force 104, the ear 100 will thereby be disposed and maintained in the "enhanced hearing orientation", as represented in FIGS. 4 and 6, as long as the base 12, 12' is in the operative position behind the ear 100.

Figure 8:
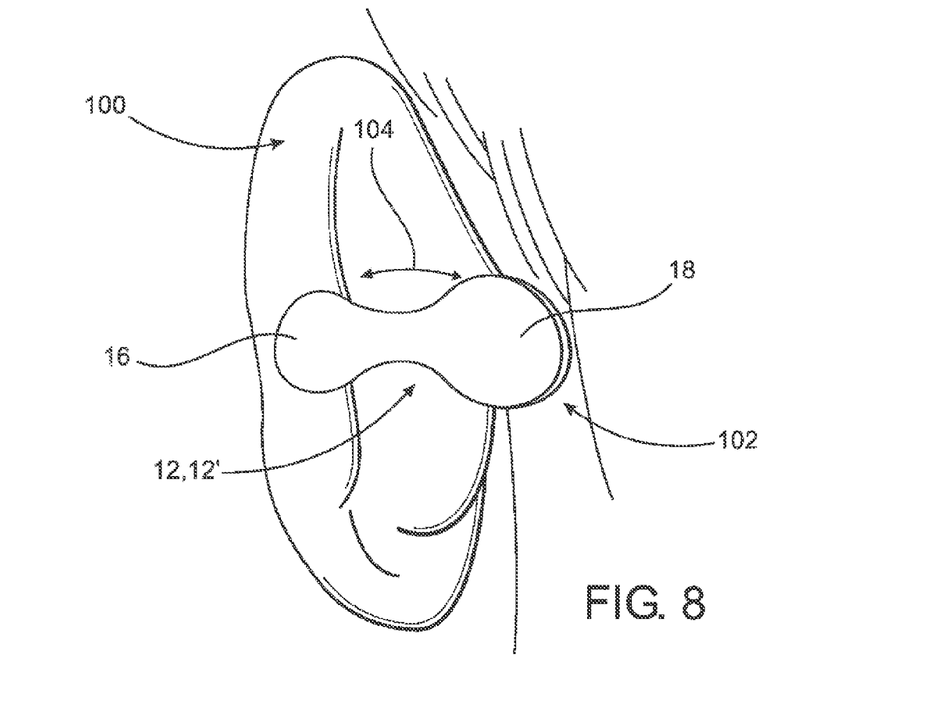
FIG. 8 is a rear view of the embodiment of FIG. 7 wherein the hearing assistance device is concurrently exerting a pushing force on the ear and the head sufficient to dispose the ear in an enhanced hearing orientation.
Figure 9:
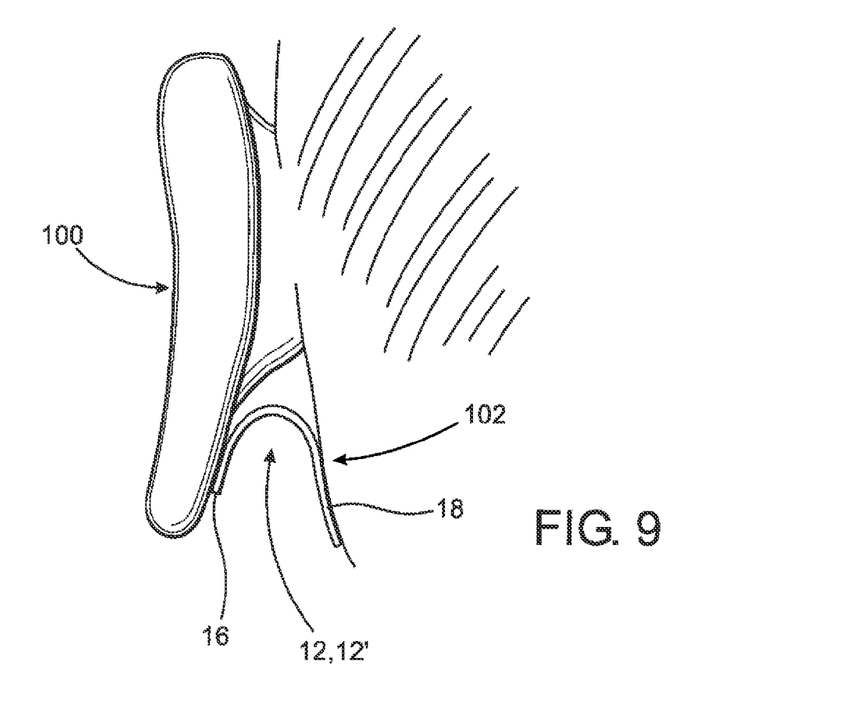
FIG. 9 is a top view of the embodiment of FIG. 7.
Figure 10:
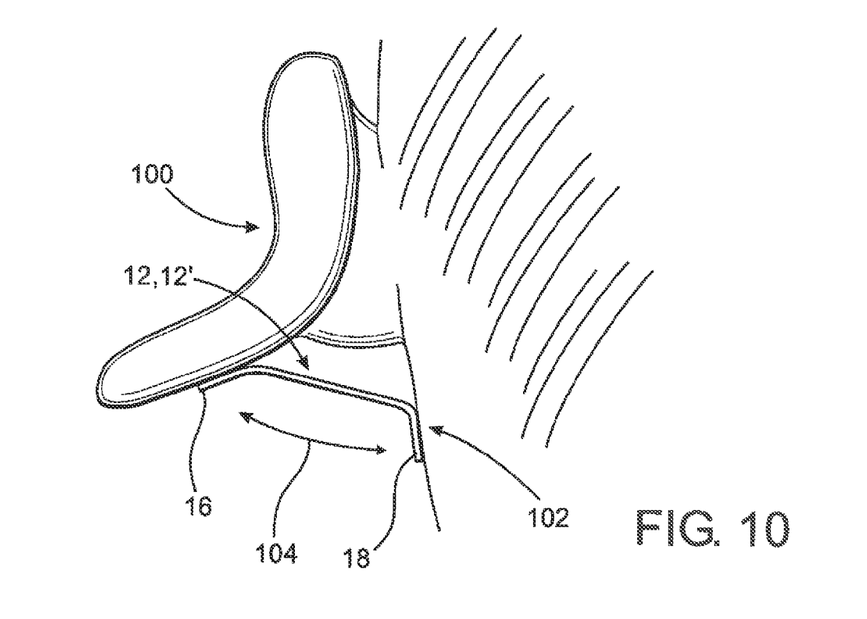
FIG. 10 is a top view of the embodiment of FIG. 8.

In more specific terms, FIGS. 4 and 6, as well as FIGS. 8 and 10 "demonstrate" the effect of the inherent bias as the base 12, 12' is biased outwardly, from an at initially curved orientation or shape as represented in FIGS. 3, 5, 7 and 9 into or at least "towards" its longitudinally extended and/or substantially linear, naturally assumed orientation. Accordingly, the presence of the aforementioned inherent bias tending to force the base 12, 12' into or towards the naturally assumed orientation and out of the at least partially curved, operative orientation or operative position of FIGS. 3, 5, 7 and 9 will result in the pushing force 104 being concurrently exerted on the rear surface of the ear 100 and the portion 102 of the head.

For purposes of additional clarification, the flexibility of the material from which the base 12, 12' is formed will allow it to be bent, folded or otherwise oriented. Therefore the base 12, 12' the biasing capability or inherent bias incorporated in the base 12, 12' allows it to be easily positioned in an "operative orientation" so as to facilitate the disposition thereof in the "operative position" represented in FIGS. 3-10. Accordingly, the "operative orientation" may at least initially assume or be defined by a curved shape or even u-shaped configuration along the length of the base to facilitate its initial disposition in the "operative position" of FIGS. 3, 5, 7 and 9. Once in this operative position, the base 12, 12' can still be accurately described as having an initially curved or even u-shaped configuration along its length, at least until the inherent bias forces it towards the outwardly extended, substantially linear, naturally assumed orientation represented in FIGS. 4, 6, 8 and 10, which results in the concurrent exertion of the pushing force 104 on the ear 100 and the portion 102 of the head.

Figure 11:
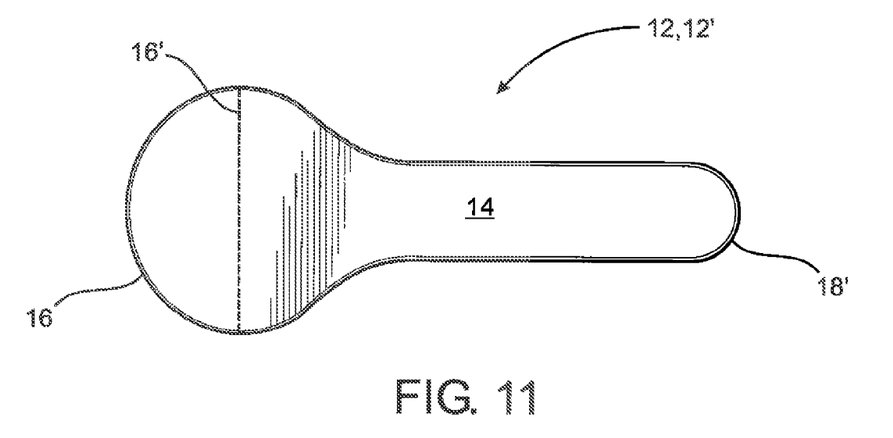
FIG. 11 is front plan view of yet another preferred embodiment of the hearing assistance device of the present invention.

With further reference to the operative position of the base 12 and 12' as represented in FIGS. 8 and 10, the ear 100 is represented in the enhanced hearing orientation. This enhanced hearing orientation is accomplished by the inherent bias incorporated within the base 12 or 12' forcing the larger or first opposite end 16 disposed in confronting engagement with the rear or backside portion of the ear 100 outwardly due, at least in part, to the flexible nature of ear 100. In contrast, the opposite or second end 18 is removably secured to the aforementioned adjacent, hard tissue portion of the head. This hard tissue portion 102 is not flexible or does not "yield" in reaction to the biasing force and/or pushing force 104 exerted thereon by the base 12 or 12'. Therefore, the biasing force or pushing force 104 concurrently exerted on the ear 100 and the portion 102 of the head, by the base 12 or 12', due to the aforementioned "inherent bias" incorporated therein, will result in the exertion of a sufficient force on the ear 100 to force it forwardly and outwardly into the hearing enhanced orientation. The concurrently directed pushing or biasing force 104 will be sufficient to dispose and maintain the ear 100 in the enhanced hearing orientation, as represented in FIGS. 9 and 11, when the base 12 or 12' is in this operative position, as described in detail above.

Moreover, the "enhanced hearing orientation" as schematically represented in the embodiments of FIGS. 4, 6, 8 and 10 will serve to enhance the hearing ability of the user of the device 10 by having a similar effect as that provided by the commonly recognized "cupping action" employed by numerous individuals which suffer from a hearing loss. Such a forwardly and outwardly directed orientation of the ear 100 disposes the interior or ear canal of the ear 100 in a better position to receive the sound waves existing in the ambient environment in which the user of the hearing assistance device 10 is located.

Figure 12:
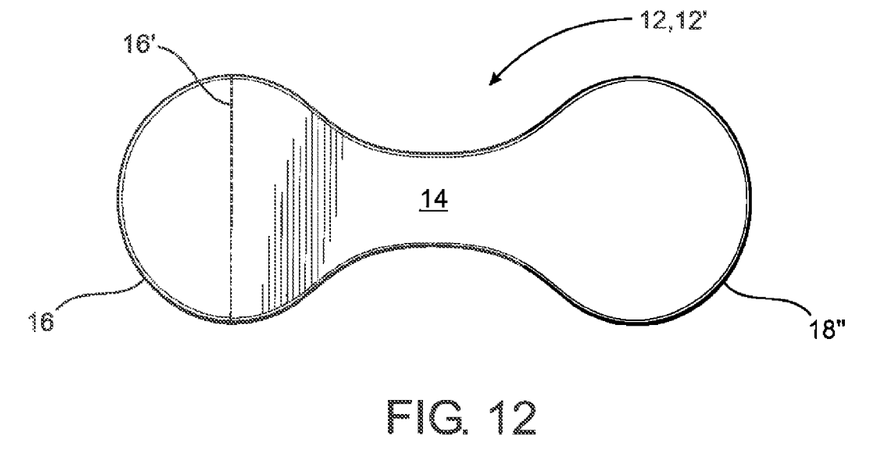
FIG. 12 is a front plan view of yet another preferred embodiment of the hearing assistance device of the present invention.

As set forth above, the hearing assistance device 10 includes the base 12 or 12' having an elongated configuration of sufficient length to selectively dispose and maintain the base 12, 12' in the operative position behind the ear 100 of the user. However, in order to further facilitate positioning of the ear in the enhanced hearing orientation of FIGS. 4 and 6, the configuration of the base 12 and 12' may vary. As represented in FIGS. 11-13, different structural configurations of the base 12 or 12' are disclosed. More specifically, the first opposite end 16 in the embodiment of FIGS. 11 and 13 has a larger overall dimension including a larger transverse dimension 16' than that of either the intermediate portion 14 or the second opposite end 18'. With regard to FIG. 10, the overall dimension of the first opposite end 16 including the transverse dimension 16' is greater than the intermediate portion 14 and substantially the same as that of the second opposite end 18'. Therefore, in the embodiments of FIGS. 1, 2, 11 and 13, the first opposite end 16 includes an overall dimension and a transverse dimension 16' which is at least as great as the second opposite end 18 and 18" and preferably greater than the second opposite end 18', as well as the intermediate portion 14.

Accordingly, a preferred embodiment of the present invention is represented in FIGS. 3-6. More specifically, the aforementioned concurrently applied pushing force 104 resulting in the forwardly and outwardly directed orientation of the ear 100, may be further facilitated by removably securing the larger and first opposite end 16 to the skin surface 102' of the corresponding hard tissue portion 102 of head. At the same time, the smaller, second opposite end 18 is secured to the backside portion of the ear 100, as clearly represented. As a result, the corresponding portion 102 of the head will effectively serve as an "anchoring base" which, due in part to its lack of flexibility, facilitates a sufficient amount of the concurrently applied pushing force 104 to be exerted on the flexible and more easily moved ear 100, so as to dispose and maintain the ear 100 in the hearing enhanced orientation of FIGS. 4 and 6. Accordingly, the larger end portion 16 mounted on the hard tissue portion 102, serving as the "anchoring base" will more efficiently distribute the pushing force 104 in a manner which assures that a sufficient force will be directed on the ear 10 to force and maintain it in the "hearing enhanced orientation".

However, as represented in FIGS. 7-10, the opposite orientation of the base 12 and/or 12' may be successively used, wherein the larger first opposite end 16 is removably secured to the portion 102 of the head and the smaller, second opposite end 18 is removably secured to the back side of the ear 100. It is assumed in this latter scenario the biasing capability of the base 12 will be sufficient to concurrently exert a sufficient biasing force or pushing force 104 to position the ear 100 in the intended hearing enhanced orientation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method for improving hearing of an individual using a hearing assistance device having a biased material base and opposite end portions, the method comprising:
   positioning the base into an enhanced hearing orientation from a naturally assumed orientation,
   disposing the base into an operative position behind an ear of the individual and assuming the hearing enhanced orientation by connecting a smaller one of the opposite end portions to a rear surface of the ear and connecting a larger one of the end portions to an adjacent head portion,
   defining the operative position as comprising each of the opposite end portions concurrently connected to a different one of the rear surface of the ear and the adjacent head portion of the individual, and
   exerting a pushing force concurrently on the rear surface of the ear and adjacent head portion, via the bias of the base, sufficient to position the ear into the enhanced hearing orientation.

2. A method as recited in claim 1 comprising disposing the ear forwardly and outwardly from the head to define the enhanced hearing orientation.

3. A method as recited in claim 1 further comprising removably connecting the opposite end portions to correspondingly disposed ones of the rear surface of the ear and the adjacent head portion.

4. A method as recited in claim 3 further comprising adhesively connecting the opposite end portions to the correspondingly disposed ones of the rear surface of the ear and the adjacent head portion.

5. A method as recited in claim 1 including defining the enhanced hearing orientation of the base as having a longitudinally curved configuration of the base.

6. A method as recited in claim 5 including defining the naturally assumed orientation of the base as comprising a substantially linear configuration of the base.

7. A method as recited in claim 5 including defining the longitudinally curved configuration of the base as a substantially U-shape configuration thereof.

8. A method as recited in claim 5 including disposing the base in the operative position and concurrently in a substantially non-observable location relative to a frontal location of the individual.

9. A method as recited in claim 1 comprising connecting the larger one of the opposite end portions to a hard tissue portion of the adjacent head portion.

10. A method as recited in claim 1 further comprising connecting the larger one of the end portions having a greater transverse dimension to the adjacent head portion to at least partially define the operative position.

11. A method as recited in claim 10 comprising connecting the greater transverse dimensioned end portion to a hard tissue portion of the adjacent head portion, when the base is in the operative position.

12. A method as recited in claim 11 comprising connecting the smaller one of the end portions having a lesser transverse dimension to the rear surface of the ear, when the base is in the operative position.

13. A method as recited in claim 10 comprising connecting the smaller one of the end portions having a lesser transverse dimension to the rear surface of the ear, when the base is in the operative position.

14. A method as recited in claim 1 comprising connecting the end portion having a lesser transverse dimension to the rear surface of the ear, when the base is in the operative position.

15. A method as recited in claim 1 comprising exerting a pushing force on the ear sufficient to establish the enhanced hearing orientation being capable of an increase of generally between 5 dB and 20 dB of sound pressure level.

* * * * *